United States Patent
Ulrich

[11] Patent Number: 5,918,377
[45] Date of Patent: *Jul. 6, 1999

[54] MOUTH WIDTH MEASURING APPARATUS

[75] Inventor: Robert A. Ulrich, Riverdale, N.Y.

[73] Assignee: Equine Oral Limited, Wilmington, Del.

[*] Notice: This patent is subject to a terminal disclaimer.

[21] Appl. No.: 08/908,569

[22] Filed: Aug. 8, 1997

Related U.S. Application Data

[63] Continuation-in-part of application No. 08/752,771, Nov. 20, 1996, Pat. No. 5,697,163, which is a continuation of application No. 08/433,000, May 2, 1995, abandoned.

[51] Int. Cl.[6] .................. G01B 5/02; G01B 3/38
[52] U.S. Cl. .................. 33/511; 33/783; 33/811; 54/7
[58] Field of Search ............... 33/511, 512, 513, 33/514, 783, 806, 810, 811, 812; 54/7, 8, 9, 6.1, 71, 1

[56] References Cited

U.S. PATENT DOCUMENTS

| | | | |
|---|---|---|---|
| 754,632 | 3/1904 | Anderson | 54/7 |
| 3,527,023 | 9/1970 | Swanson | 54/8 |
| 4,718,850 | 1/1988 | Knebelman | 33/513 |
| 4,843,720 | 7/1989 | Kim | 33/513 |
| 5,158,096 | 10/1992 | Clark et al. | 33/514 |
| 5,697,163 | 12/1997 | Ulrich | 33/511 |

FOREIGN PATENT DOCUMENTS

| | | | |
|---|---|---|---|
| 1064364 | 5/1954 | France | 33/810 |
| 2319 | 2/1878 | Germany . | |
| 302209 | 12/1928 | United Kingdom . | |
| 1184341 | 3/1970 | United Kingdom | 54/8 |

*Primary Examiner*—Christopher W. Fulton
*Attorney, Agent, or Firm*—King and Schickli

[57] ABSTRACT

An apparatus is provided for measuring the width of the mouth of a horse or other domesticated farm animal so as to allow one to select a bit of suitable width. The apparatus includes a crossbar having first and second ends, a first annular stop received on the crossbar adjacent the first end and a second annular stop received on the crossbar adjacent the second end. At least one of the stops slides along the crossbar. The width of the horse's mouth is measured by engaging a first side of the mouth of the horse with the first stop and a second side of the mouth of the horse with the second stop and measuring the distance therebetween along the crossbar. Central openings in the annular stops receive and accommodate any wrinkled flesh around the margin of the mouth are the apparatus is positioned to complete the measurement of the mouth. This insures accurate width measurement.

13 Claims, 5 Drawing Sheets

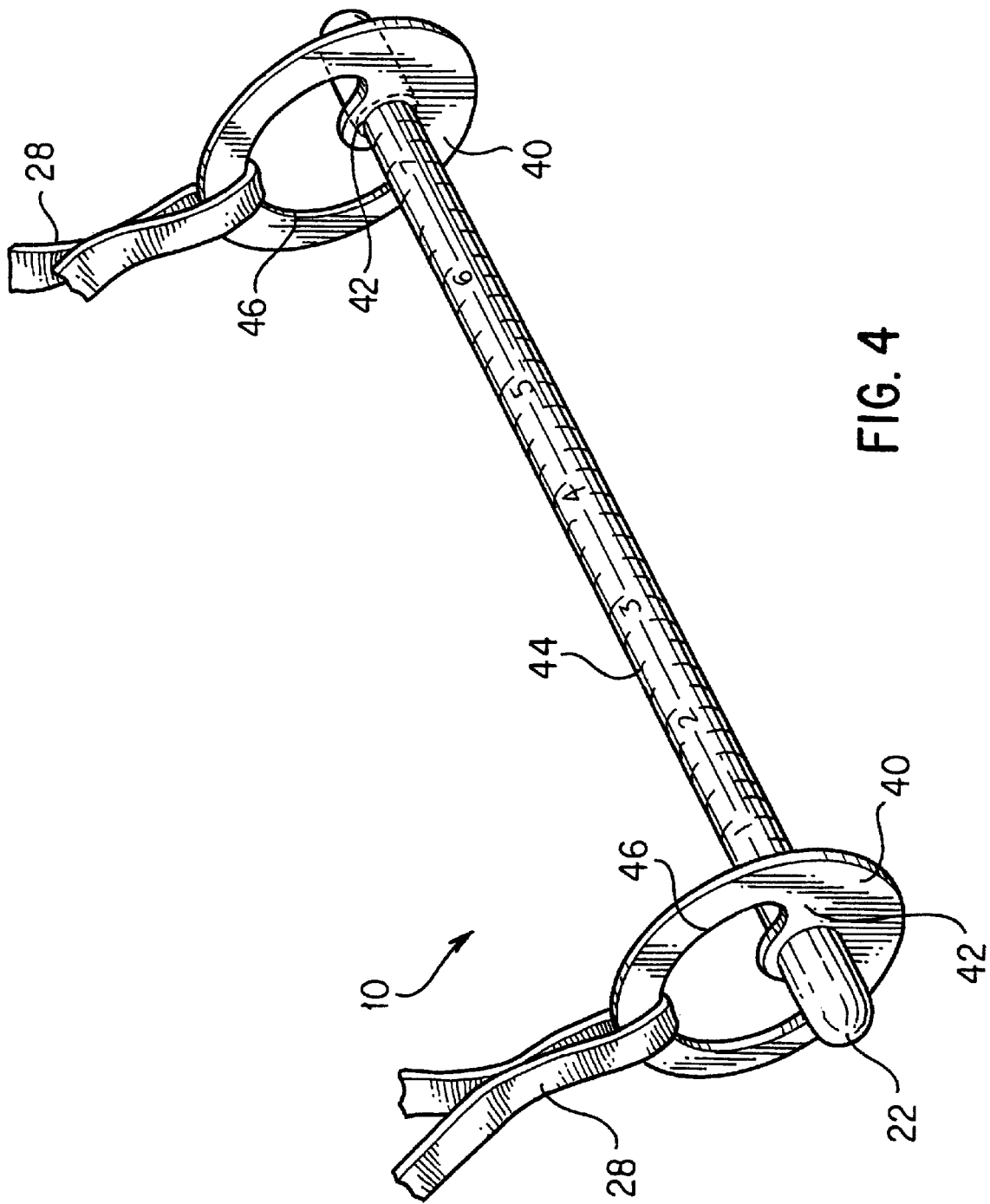

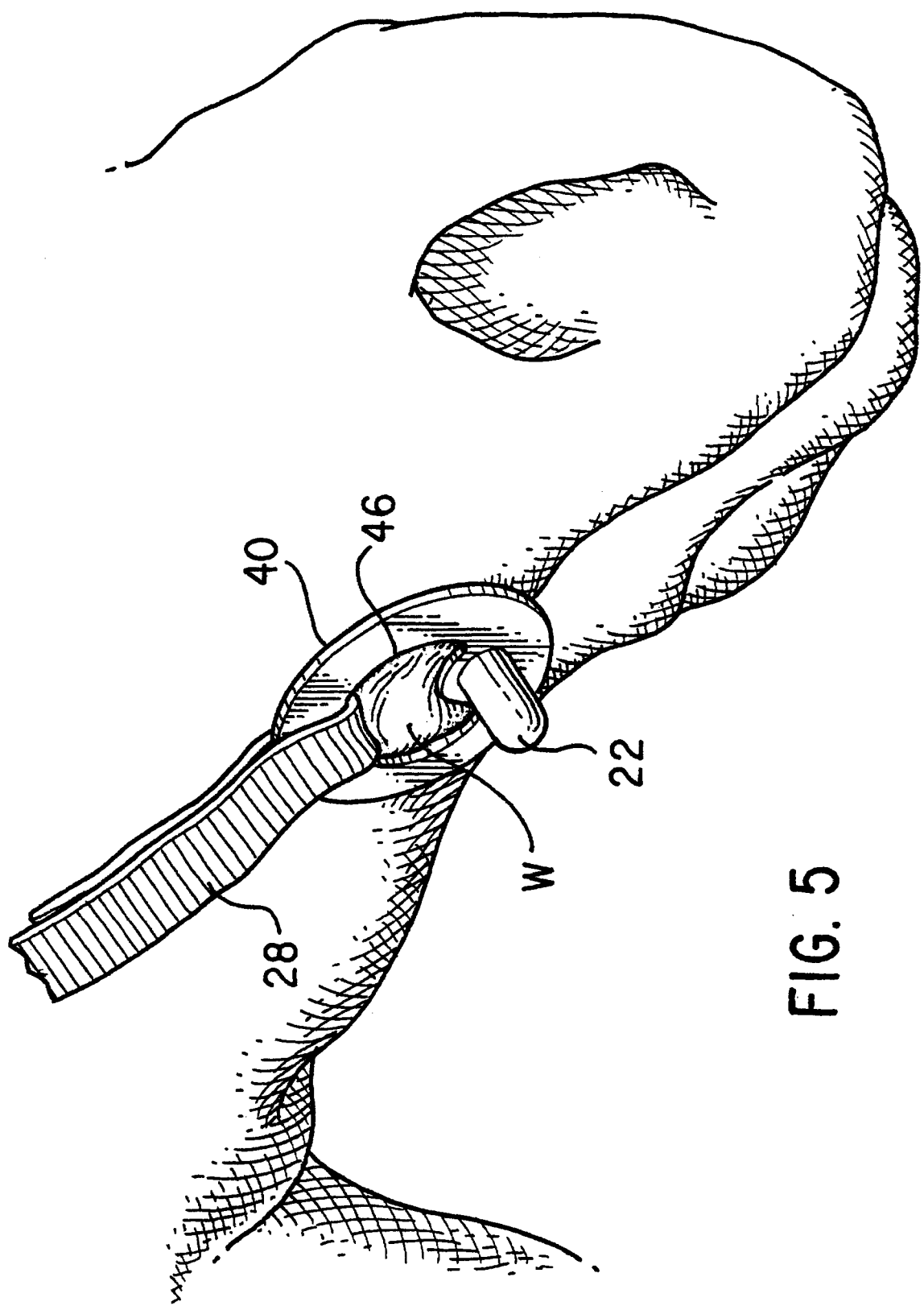

MOUTH WIDTH MEASURING APPARATUS

This application is a continuation-in-part of U.S. application Ser. No. 08/752,771, filed Nov. 20, 1996, now issued U.S. Pat. No. 5,697,163, which is a continuation of application Ser. No. 433,000, filed May 2, 1995, now abandoned.

TECHNICAL FIELD

The present invention relates generally to the care and management of domesticated livestock, such as horses and, more particularly, to an apparatus and method for measuring the mouth width of a horse or other animal.

BACKGROUND OF THE INVENTION

Horses have been one of the most useful animals for man for thousands of years. At one time horses provided man with the fastest and most effective means of land transportation. While long since replaced by trains, automobiles, trucks and motorcycles as a means of land transportation, horses are still used by thousands of people for recreation, sport and work. Horses are ridden by adults and children alike for fun and exercise. Horses perform at rodeos, circuses, parades, horse shows and race tracks. They are used by ranchers to herd cattle and other livestock and may be used to pull plows and wagons and do other farm work.

In any of these tasks and uses, the horse is controlled by means of a bridle. The bridle consists of (1) a bit, such as a horizontal metal bar placed in the mouth of the horse, (2) a series of straps known as the headstall that fit about the head of the horse and hold the bit in position and (3) reins that are held in the hand of the rider or driver and used to control the horse. More specifically, the reins are connected to either side of the bit and are used to communicate with and direct the animal.

In order to maximize both the comfort of the horse and rider control, a bit should be selected that is of a length substantially corresponding to the width of the mouth of the horse. A bit that is too short will simply not be properly received in the mouth of the horse. A bit that is too long may lead to injury and often will fail to provide the best "signal" to the horse when the reins are manipulated and, hence, there is some compromise in rider control.

In the past, a trial and error method has been used to fit a horse for a bit. Specifically, a bridle with a bit of a certain size is selected and properly positioned on the horse. If the bit proves to be too short or too long, that bridle may be removed and the bit is replaced with a shorter or longer size as necessary. This procedure may have to be repeated several times to identify a bit of proper width for the horse. It should be appreciated that this is a time consuming and inconvenient procedure. The present invention seeks to simplify this process.

SUMMARY OF THE INVENTION

Accordingly, the primary object of the present invention is to provide an apparatus and method for actively measuring the mouth width of a horse, mule or other domesticated farm animal to allow one to select a bit of proper width while overcoming the above described limitations and disadvantages of the prior art.

Another object of the present invention is to provide a simple and inexpensive apparatus for measuring the width of an animal's mouth to allow one to size a bit that is easy to use and provides accurate results.

Still another object of the present invention is to provide a quick, efficient and simple method for accurately assessing the width of a horse's mouth and jawline so that the proper size bit may be selected for the horse the first time without a need for a trial and error approach to the problem.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, a novel and unique apparatus is provided for measuring a horse's mouth and selecting a bit of proper width. The apparatus includes an elongated crossbar having first and second ends. A first stop, in the form of an annular disc or plate with a central opening is received on the crossbar adjacent to the first end. A second, similar stop also in the form of a disc or plate, is received on the crossbar adjacent to the second end. At least one of these stops is mounted for sliding engagement along the crossbar.

This apparatus may be effectively utilized in one of several ways to accurately measure the width of the horse's mouth. This makes it possible to readily select a bit of proper width to be utilized in the bridle for the horse. Specifically, the crossbar may be positioned under the mouth just rearwardly of the chin so as to extend traversaly across the mouth between the left and right sides. One stop is engaged on each side of the mouth. The apparatus may then be removed and the distance along the crossbar between the stops measured.

Still more accurate determination may be made by positioning the crossbar within the horse's mouth. The stops may then be positioned against each of the two opposing sides of the mouth. The crossbar is then pushed back into the position occupied by a bit during riding so as to produce a slight "smile" of the horse's mouth. Any wrinkling flesh occurring around the margin of and projecting outwardly from the mouth is received in and fully accommodated by the central opening in each stop. As a result, any tendency of the mouth margin wrinkling to spread the stops is avoided. Thus, this interference with accurate mouth width measurement and, therefore, accurate bit size determination is fully overcome. The apparatus is then removed and once again, the distance between the two stops along the crossbar is measured. With either approach, this measured distance provides an accurate indication of the width of the mouth to thereby allow one to select the proper size bit to be incorporated into the bridle for the horse.

More preferably, the crossbar of the apparatus includes graduations. As bits are marketed in various places in the world in widths designated by inches or centimeters, the graduations may be in inches and/or centimeters. Additionally, the first stop may be fixed to the crossbar adjacent a first end designated as the "0" graduation. Thus, when the crossbar is positioned to measure the width of the mouth with the first stop against one side of the mouth and the second stop against the other, the width measurement is indicated on the crossbar by the position of the second stop on the graduation scale. Accordingly, it is possible to quickly and conveniently determine the proper size bit required to best suit the horse and thereby provide the utmost comfort to the horse while also promoting superior rider control.

In accordance with yet another aspect of the present invention, the crossbar is preferably a curved or straight rod of hard plastic, polymer (e.g. LEXAN) or metal (e.g. steel) having a circular section of a diameter between preferably 0.25 and 0.75 inches. Accordingly, the crossbar assumes a bit-like position in the mouth of the horse during measurement. Such crossbar materials are also sufficiently strong to resist damage when, for example, a horse bites down on the crossbar. They also require minimal care and provide for a long service life.

Additionally, caps may be provided on each end of the crossbar. Preferably, the caps include an inner edge, face or shoulder of greater effective diameter than the crossbar. Advantageously, by sizing the stops to include apertures providing sufficient clearance to be received over the crossbar but smaller in diameter than the face or the shoulder of the end caps, the stops are effectively captured on the crossbar. In this way, the risk of misplacing or losing one of the stops is effectively eliminated.

In accordance with still another aspect of the present invention, each of the stops may include an elongated segment having slots or other means for engaging a strap. Preferably, a strap of, for example elastic or nylon, is provided. This strap forms a loop extending from one stop to the other. When measuring the width of the horse's mouth, this loop may be pulled back over the poll of the horse's head so as to secure the crossbar in the horse's mouth in a bit receiving position during measurement. With some horses, this aides the individual in the measuring process. Of course, it should be appreciated that the ends of the strap may be made adjustable by including hook and loop fasteners such as VELCRO brand fasteners or some other means.

In accordance with yet another aspect of the present invention and as mentioned above, a method of fitting a horse for a bit is also provided. The method includes the steps of positioning the crossbar adjacent to the mouth of the horse, bringing the first stop into engagement with the first side of the mouth of the horse, moving the second stop into engagement with the second side of the mouth of the horse and measuring the distance along the crossbar between the first and second stops. Preferably, the crossbar is actually placed in the mouth of the horse. Additionally, the crossbar is preferably pressed back into the mouth so as to assume the position assumed by a bit during use.

As further discussed above, a strap may be attached to the ends of the first and second stops. The strap may be looped over the head of the horse so as to stretch across the poll behind the ears. In this way, the crossbar is positively held in the mouth of the horse so as to be positioned in the manner of a bit during the measuring process. This allows a most accurate measurement to be made for fitting the bit for the horse.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawing incorporated in and forming a part of the specification, illustrates several aspects of the present invention and together with the description serves to explain the principles of the invention. In the drawing:

FIG. 4 is a perspective view of an alternative embodiment of the apparatus including annular stops; and FIG. 5 is a detailed perspective view showing how the central opening in an annular stop accommodates mouth margin wrinkles when the apparatus is positioned like a bit to measure the width of a horse's mouth.

Reference will now be made in detail to the present preferred embodiment of the invention, an example of which is illustrated in the accompanying drawing.

DETAILED DESCRIPTION OF THE INVENTION

Figure 1:
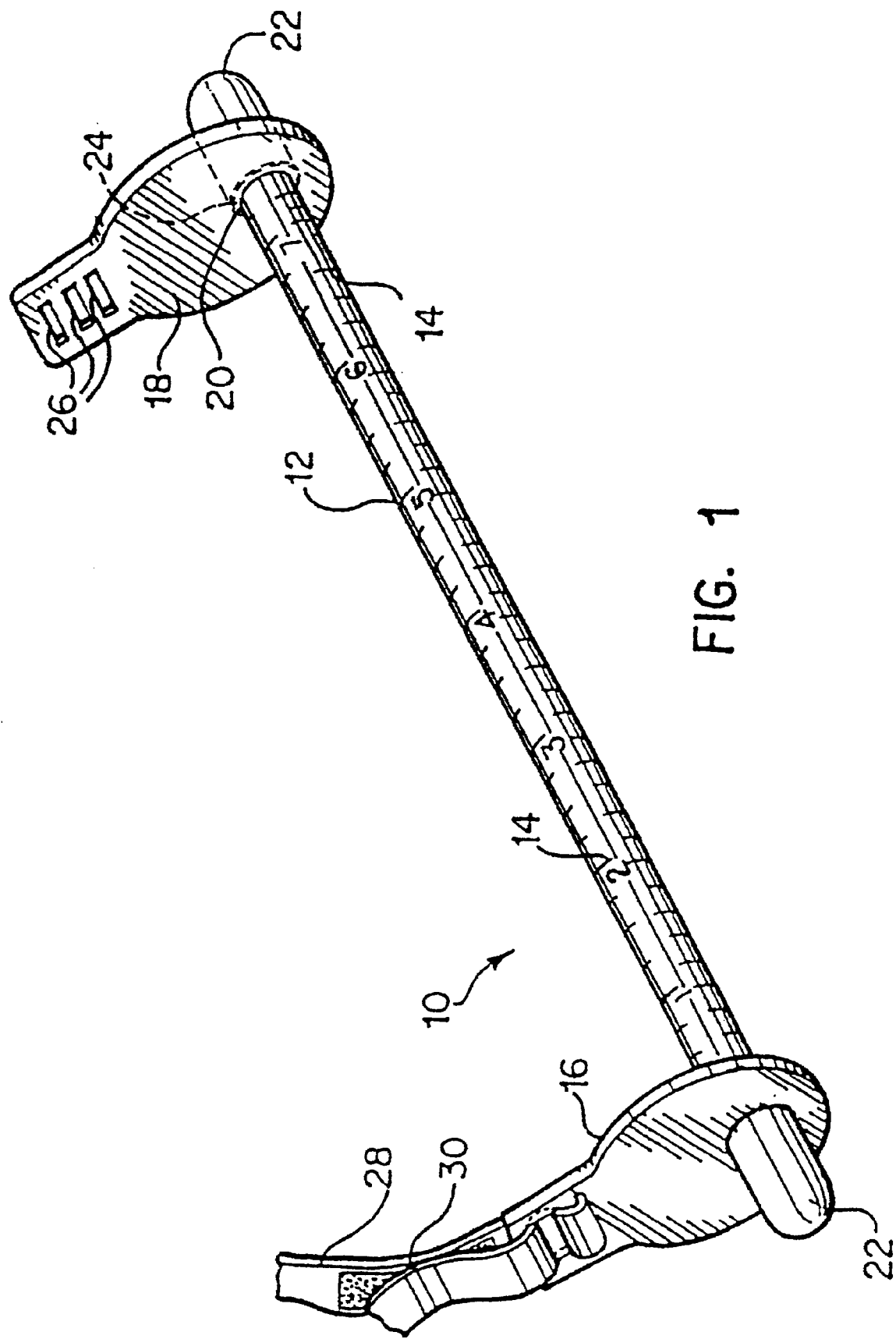
FIG. 1 is a perspective view of the apparatus of the present invention.

Reference is now made to FIG. 1 showing the apparatus 10 of the present invention for measuring a horse, mule or other domesticated farm animal for a bit. As shown, the apparatus 10 includes an elongated straight or curved crossbar 12, preferably including graduations 14 for purposes of measuring length. Preferably, the crossbar 12 is formed from a hard, durable plastic (e.g. an acrylic such as LEXAN). Such a material is strong enough to resist damage when, for example, a horse bites down on the crossbar 12 while also requiring minimal maintenance or care over a long service life. A metal crossbar 12 of, for example, steel could also be used. Preferably, the graduations 14 are in inches and/or centimeters, the two measuring systems utilized to categorized the size of bits throughout the world.

A pair of stops 16, 18 are positioned on the crossbar 12. As shown each stop 16, 18 includes a mounting aperture 20 of sufficient size to just receive the crossbar 12. The first stop 16 may be fixed to the crossbar 12 by adhesive or some other means at the "0" graduation. In contrast, the second stop 18 is mounted to allow sliding movement along the crossbar 12 to better allow the measurement of the width of the horse's mouth as described in greater detail below. Preferably, the stops 16, 18 are made from a clear hard plastic, such as acrylic, so as to allow one to see through the stops and observe the mouth of the horse. This is important during the bit sizing process as described below.

End caps 22 may be secured to the ends of the crossbar 12. As shown the end caps 22 present an inner edge, face or shoulder 24 of greater diameter than the crossbar 12 and apertures 20 in the stops 16, 18. In this way, the stops 16, 18 are captured on the crossbar 12 so that they may not be inadvertently lost or misplaced.

As further shown in FIG. 1, each of the stops 16, 18 includes one or more spaced slots 26 or other means for engaging a strap 28. Thus, it should be appreciated that the stops 16, 18 may take the form of a disc or plate of substantially key hole shape. The ends of the strap 28 are laced through the spaced slot(s) 26 and secured by hook and loop fasteners (e.g. VELCRO fasteners) or some other appropriate means. This also allows the length of the strap 28 to be adjusted as desired. Preferably, the strap 28 provides some tension to hold the apparatus 10 in place during the fitting of a horse for a bit as will now be described.

In the alternative embodiment shown in FIGS. 4 and 5, the stops are annular. Specifically, the alternative embodiment of the stop 40 includes an aperture 42 of sufficient size to receive the cross bar 44 and a central opening 46. The opening 46 not only allows direct viewing to confirm proper placement of the apparatus 10 but also accommodates the wrinkled margin W of the mouth of the horse when the apparatus is positioned to measure mouth width. A more accurate measurement is possible since the central opening 46 has sufficient clearance to receive the wrinkled margin W of the mouth which therefore does not interfere with and press the stops outward so as to alter the width measurement.

The apparatus 10 is relatively easy to use. Preferably, the head of the horse is tethered to each side of a stall or barn doorway in a manner well known to those who handle horses. The second stop 18 is then displaced or moved toward the second end of the crossbar 12 opposite the first stop 16 that may be secured to the first end thereof. The crossbar 12 is then positioned in the mouth of the horse so that the first stop 16 engages one side of the horse's mouth. The individual then slides the second stop 18 into engagement with the other side of the horse's mouth. The crossbar 12 is then removed from the horse's mouth while marking the position of the second stop. The distance along the crossbar 12 between the first and second stops 16, 18 is then measured by referring to the graduations 14. Specifically, the graduation 14 at the second stop 18 is a direct indication of the width of the horse's mouth. This information may then be utilized to select the most appropriate width bit for the horse's bridle.

It should be appreciated that this is done in one simple procedure eliminating any need for trial and error. Advantageously, by utilizing the present invention, it is possible to fit the horse with the best possible size bit. This increases the comfort for the horse and, accordingly, the horse maintains greater sensitivity to rein commands over a longer period of time. Oversized bits have a tendency to slide in the horse's mouth, thereby pinching the tongue or cheek and causing injury. The risk of this occurring is substantially eliminated. Further, with improved horse comfort and better sensitivity to rein commands, the present invention also allows enhanced rider control.

Figure 2:
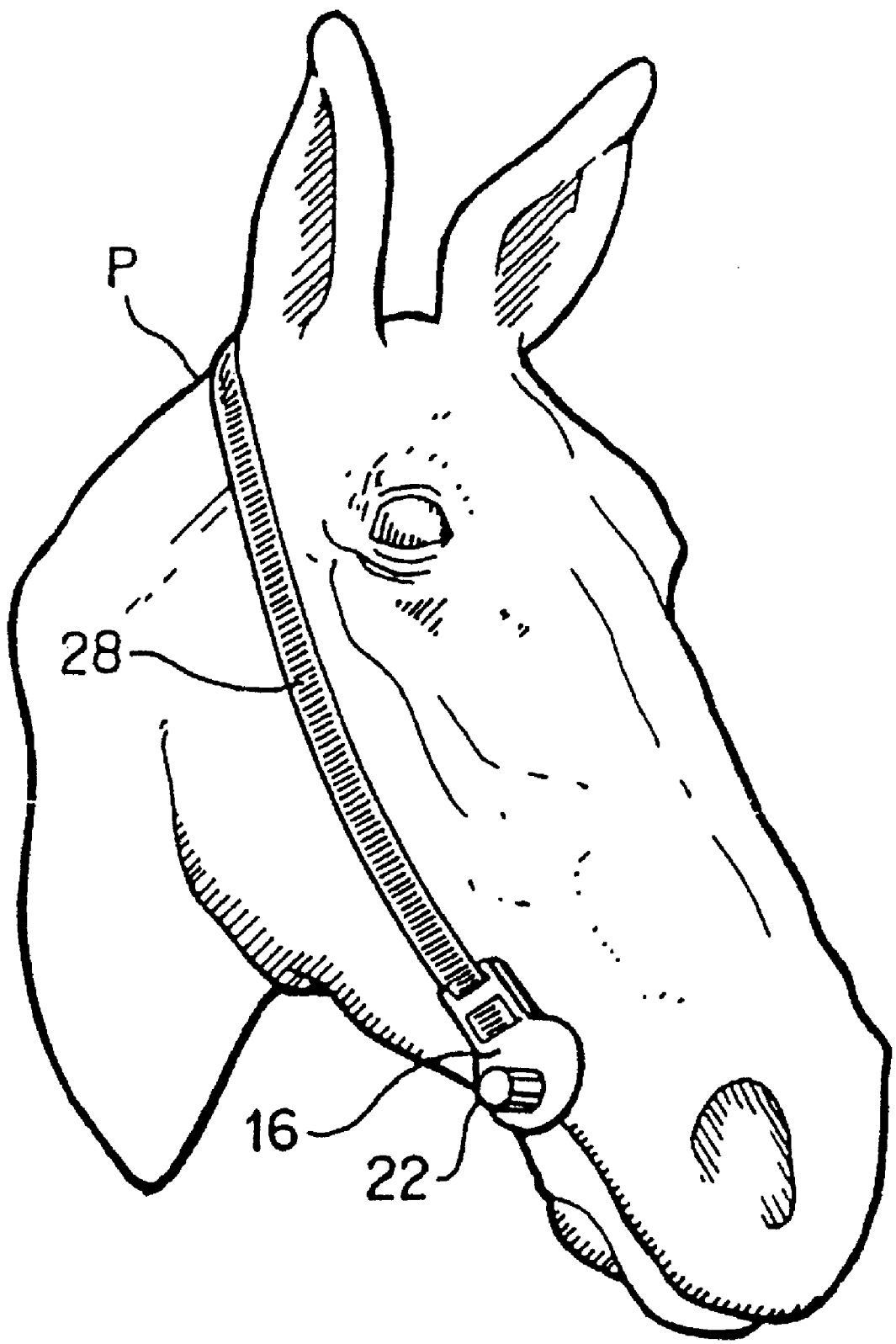
FIG. 2 is a perspective view illustrating the method of measuring the width of a horse's mouth utilizing the apparatus of FIG. 1.

With certain horses, such as those of higher spirit that are difficult to handle and/or competition horses where performance must be maximized, it may be desired to use the strap 28 during the measuring process. In this situation, the stops 16, 18 are spread and the crossbar 12 is placed in the mouth of the horse just as previously described. The strap 28 is then pulled up over the ears of the horse so as to extend across the poll P (see particularly FIG. 2). The goal is to hold the crossbar 12 pressed back into the mouth of the horse so that the crossbar assumes substantially the same position a bit would assume in the mouth of the horse during riding. By adjusting the length of the strap 28 through operation of the hook and loop fasteners 30, the resilient strap may provide the desired force to hold the crossbar 12 in position. This may be checked by visually confirming the horse's "smile" when looking through the transparent stops 16, 18. Of course, the crossbar 12 is preferably 0.25 and 0.75 inches in diameter so as to generally mimic the shape of the bit in the horse's mouth and thereby provide a more accurate measurement.

Figure 3:
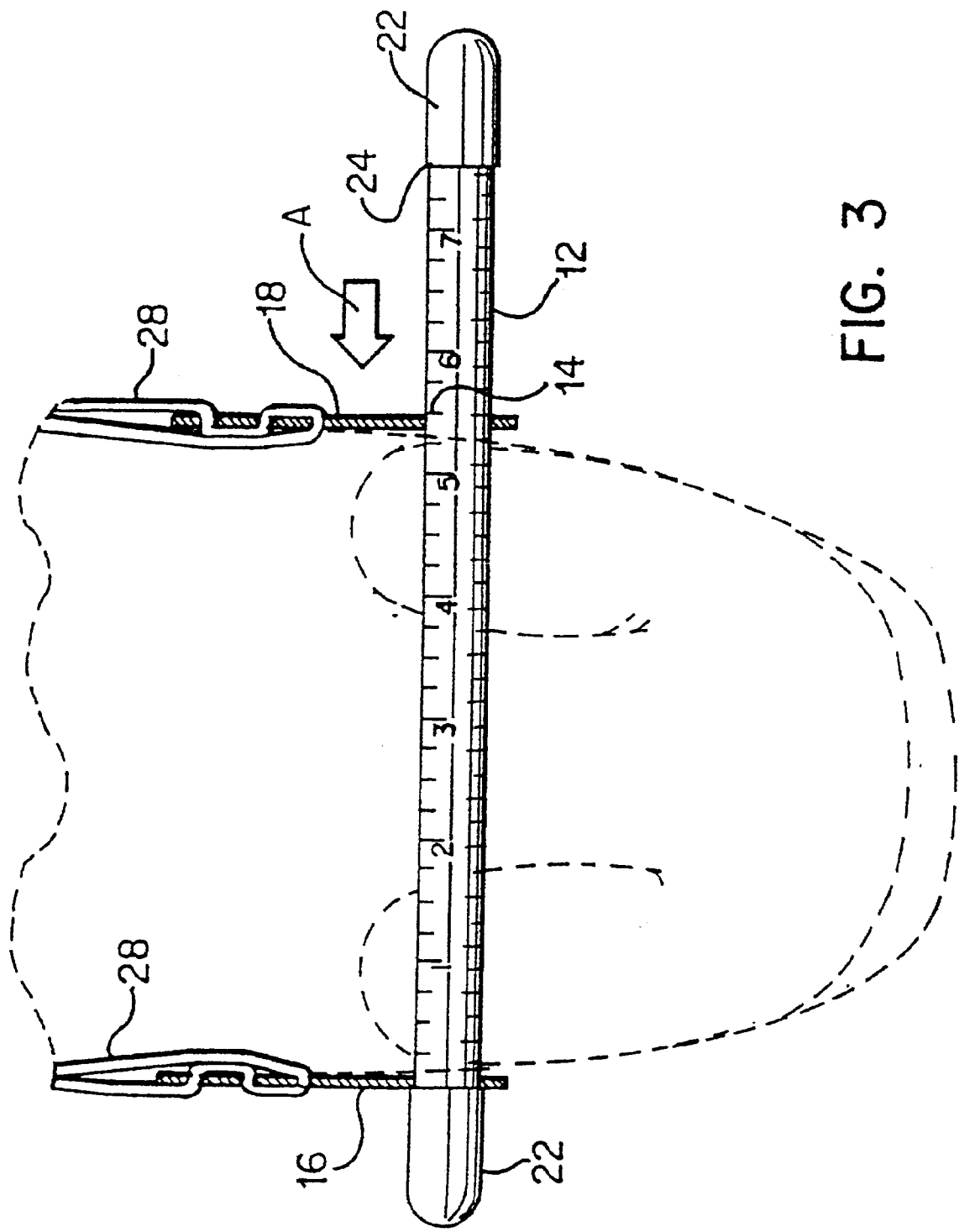
FIG. 3 is a detailed front elevational view with the muzzle of the horse shown in phantom to further illustrate the measuring method also illustrated in FIG. 2.

With the strap 28 adjusted to properly position the crossbar 12, the position of the apparatus 10 may be adjusted to insure that the first stop 16 engages one side of the horse's mouth. Next the individual confirms that the second stop 18 engages with the other side of the horse's mouth (note particularly, FIG. 3 and action arrow A). The graduation at the second stop may be read at this time to determine the width of the horse's mouth or the apparatus 10 may be removed from the horse while holding the second stop in position and then making a reading.

The method of measuring a horse for a bit described above and shown in drawing FIGS. 2 and 3 is a preferred method. It should be appreciated, however, the invention is not limited to the precise procedure described. For example, while perhaps less accurate, the apparatus 10 may be utilized to measure the width of the mouth without positioning the crossbar 12 in the mouth. For example, the crossbar 12 may be positioned under the lower jaw with the two stops 16, 18 brought together until they engage each side of the mouth. The graduation 14 at the second stop 18 is then read to make a width determination.

In summary, numerous benefits result from employing the concepts of the present invention. For the first time, it is now possible to effectively and accurately measure the width of the mouth of a horse in order to provide the horse with a properly fitting bit. Advantageously, a properly sized bit provides a number of significant benefits including an increase in the horse's comfort, a reduction in the risk of injury to the horse resulting from the use of an improper size bit, and an increase in sensitivity to rein commands thereby improving rider control. Advantageously, the method is relatively quick and simple and far less time consuming and far more convenient than the trial and error method utilized in the past wherein various size bits are placed in the mouth of the horse to determine the best size.

The foregoing description of a preferred embodiment of the invention has been presented for purposes of illustration and description. It is not intended to be exhaustive or to limit the invention to the precise form disclosed. Obvious modifications or variations are possible in light of the above teachings. For example, a clamp or clip may be utilized to secure the second stop in the measurement position (i.e. in the position where the second stop engages the side of the horse's mouth) just before the crossbar 12 is removed from the horse's mouth. This allows the individual to accurately confirm the width measurement at the convenience of the individual after the apparatus 10 has been removed from the mouth of the horse. Additionally, the annular stop may take another shape so long as a clearance space is maintained to accommodate the projecting flesh of a mouth wrinkle when the device is positioned like a bit to measure mouth width.

The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

I claim:

1. An apparatus for measuring the width of the mouth of a domesticated farm animal to allow one to select a bit of proper width comprising:

a graduated crossbar having a first end and a second end;

a first stop received on said crossbar adjacent said first end; and a second stop received on said crossbar adjacent said second end, at least one of said first and second stops being mounted for sliding movement along said crossbar whereby the width of the mouth of the domesticated farm animal may be measured by engaging each side of the mouth of the domesticated farm animal with said first and second stops and measuring the distance therebetween along the crossbar;

said apparatus being further characterized by each of said first and second stops including an open space providing necessary clearance to accommodate any projecting mouth margin that results from placement of said apparatus in the mouth of said domesticated farm animal.

2. The apparatus set forth in claim 1, wherein each of said first and second stops is substantially annular.

3. The apparatus set forth in claim 2, wherein said first stop is fixed adjacent said first end of said crossbar at a "zero" graduation.

4. The apparatus set forth in claim 3, wherein said graduations are in inches.

5. The apparatus set forth in claim 3, wherein said graduations are in centimeters.

6. The apparatus set forth in claim 3, wherein said graduations are in inches and centimeters.

7. The apparatus set forth in claim 3, further including end caps on said first and second ends of said crossbar to engage and maintain said first and second stops on said crossbar.

8. The apparatus set forth in claim 7, wherein said first and second stops include means for engaging a strap and said apparatus includes a strap for positioning over a poll of the domesticated farm animal to hold said apparatus in position during use.

9. The apparatus set forth in claim 8, wherein said crossbar is a rod having a circular section of a diameter between 0.25 and 0.75 inches.

10. The apparatus set forth in claim 1, wherein said first stop is fixed adjacent said first end of said crossbar.

11. The apparatus set forth in claim 1, further including end caps on said first and second ends of said crossbar to engage and maintain said first and second stops on said crossbar.

12. The apparatus set forth in claim 1, wherein said first and second stops include means for engaging a strap and said apparatus includes a strap for positioning over a poll of the domesticated farm animal to hold said apparatus in position during use.

13. The apparatus set forth in claim 12, wherein said crossbar is a rod having a circular section of a diameter between 0.25 and 0.75 inches.

* * * * *